United States Patent [19]

Camaggi et al.

[11] Patent Number: 5,385,892

[45] Date of Patent: Jan. 31, 1995

[54] ETHYLAMINO PHENYL ETHERS HAVING ANTIFUNGAL ACTIVITY

[75] Inventors: Giovanni Camaggi, Novara; Lucio Filippini, Saronno; Marilena Gusmeroli, Monza; Carlo Garavaglia, Cuggiono; Luigi Mirenna, Milan, all of Italy

[73] Assignee: Ministero Dell "Universita" E Dell Ricerca Scientifica E Tecnologica, Italy

[21] Appl. No.: 1,919

[22] Filed: Jan. 4, 1993

Related U.S. Application Data

[63] Continuation of Ser. No. 667,920, Mar. 11, 1991, abandoned.

[30] Foreign Application Priority Data

Mar. 13, 1990 [IT] Italy ................... 19653 A/90

[51] Int. Cl.$^6$ ............. C07D 295/088; C07D 413/12; C07F 7/10; A61K 31/695
[52] U.S. Cl. ............................. 514/63; 514/227.5; 514/227.8; 514/231.5; 514/235.5; 514/239.2; 544/59; 544/60; 544/69; 544/111; 544/124; 544/174; 546/14; 546/236; 556/413; 564/353; 564/354
[58] Field of Search ............... 544/59, 60, 69, 111, 544/124, 174; 514/63, 227.5, 227.8, 231.5, 235.5, 239.2

[56] References Cited

U.S. PATENT DOCUMENTS 4,393,061  7/1983  Yu .......................... 544/174

FOREIGN PATENT DOCUMENTS 2754029  6/1978  Germany ................... 544/174

OTHER PUBLICATIONS

"The Pesticide Manual", 7th Edition, Published by the British Cropo Protection Council, p. 6220, (1983).

*Primary Examiner*—Mukund J. Shah
*Assistant Examiner*—P. I. Datlow
*Attorney, Agent, or Firm*—Morgan & Finnegan

[57] ABSTRACT

The ethylamino phenyl ethers of the invention and compositions thereof are endowed with high activities as inhibitors of the growth of several species of pathogen fungi and are applied to plants or to plant parts and are effective in preventing the diseases caused by pathogen fungi, such as, e.g., those belonging to Erysiphe and Helminthosporium genera.

19 Claims, No Drawings

ETHYLAMINO PHENYL ETHERS HAVING ANTIFUNGAL ACTIVITY

This is a continuation of co-pending application Ser. No. 07/667,920, filed on Mar. 11, 1991 now abandoned.

FIELD OF THE INVENTION

The present invention relates to aminic compounds endowed with a high fungicidal activity, to the process for producing them and to their use in the agricultural field as fungicides.

Therefore, the object of the present invention are the compounds having the general formula:

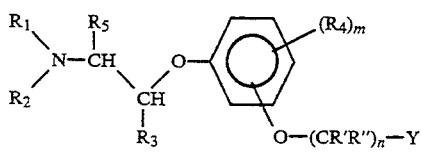
(I)

wherein:
- $R_1$ and $R_2$, which may be either equal to, or different from, each other, represent H atoms, either linear or branched $(C_1-C_6)$-alkyl groups, Ar—B groups in which
  - Ar is a $(C_6-C_{10})$-aryl or $(C_6-C_{10})$-halo-aryl group and
  - B is a $(C_1-C_4)$-alkylene or $(C_1-C_2)$-alkyl-$(C_1-C_4)$-alkylene group,
  - or, taken together with each other and together with the N atom, Ar and B represent a $(C_3-C_8)$-heterocyclic group or a $(C_2-C_7)$-heterocyclic group containing a second heteroatom selected from among O and S, with said heterocyclic groups being optionally substituted with one or more $(C_1-C_4)$-alkyl groups, $(C_6-C_{10})$-aryl groups, Ar—B groups as defined above, and halogens;
- $R_3$ and $R_5$, which may be either equal to, or different from, each other, represent H atoms, $(C_1-C_3)$-alkyl groups, or jointly form an either linear or branched $(C_1-C_7)$-alkylene group;
- m is an integer of from 0 to 4;
- $R_4$ which, when m is higher than 1, may be either different from, or equal to, one another, represent halogen atoms, $(C_1-C_3)$-alkyl groups or $(C_1-C_3)$-halo-alkyl groups;
- $R'$, $R''$, which may be either equal to, or different from, each other, represent H, $(C_1-C_3)$-alkyl group, halogen atoms;
- n is an integer comprised within the range of from 0 to 3;
- Y represents a —CH=CH$_2$ group, a $(C_3-C_6)$-cycloalkyl group, a $(C_6-C_{10})$-aryl group, a 5- or 6-membered heterocyclic group, and said groups can be optionally substituted with one or more halogen atoms, $(C_1-C_4)$-alkyl groups, $(C_1-C_2)$-haloalkyl groups, $(C_1-C_3)$-alkoxy groups, $(C_1-C_3)$-halo-alkoxy groups; or represents a $$-\text{Si}\begin{matrix}\diagup C \\ -D \\ \diagdown E\end{matrix}$$

group in which

C, D, E, either equal to, or different from, one another, represent H atoms, $(C_1-C_4)$-alkyl groups, $(C_1-C_4)$-haloalkyl groups, $(C_1-C_4)$-alkoxy groups, $(C_1-C_4)$-halo-alkoxy groups, $(C_6-C_{10})$-aryl groups, and $(C_6-C_{10})$-haloaryl groups.

The compounds of general formula (I) contain at least one center of asymmetry: the synthesis and use of pure enantiomers or of pure diastereoisomers, as well as mixtures thereof in any ratios, falls within the scope of the instant invention.

In the disclosure of the instant invention, by "halogens" atoms of F, Cl, Br and I are meant.

Examples of aryl groups are the phenyl group, the naphthyl group and higher homologues.

Examples of Ar—B groups are benzyl and 3-phenyl-propyl.

Examples of

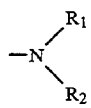

groups, when $R_1$ and $R_2$, together with each other, represent a $(C_3-C_8)$- or $(C_2-C_7)$-heterocyclic group as defined hereinabove, are those groups which derive from 2,6-dimethyl-morpholine, morpholine, piperidine, 2,6-dimethylpiperidine, thiomorpholine, and so forth. They can also be substituted as defined above.

Examples of heterocyclic Y groups of 5 or 6 members are: pyridines, pyrimidines, thiophenes, thiazoles, oxazoles, isoxazoles and their derivatives containing fused benzene rings, and containing such substituents as defined above.

Among the Y groups meaning $(C_3-C_6)$-cycloalkyl groups, the cyclohexyl, cyclopropyl, cyclopentyl, cyclobutyl groups, also substituted as defined above, such as 1-methyl-2,2-dichloro-cyclopropyl, may be mentioned.

Among the silyl groups, trimethyl-silyl, tert.-butyl-dimethyl-silyl and dimethyl-phenyl-silanyl groups, and so forth, may be mentioned. The following are further objects of the present invention:

- the salts of the compounds of general formula (I) deriving from an inorganic acid, such as a hydrogen halide acid, for example: hydriodic, hydrobromic, hydrochloric acids, sulfuric acid, nitric acid, thiocyanic acid and phosphoric acid; or from an organic acid, such as acetic acid, propanoic acid, ethane-dicarboxy acid, propane-dicarboxy acid, benzoic acid, salicylic acid, saccharin, methanesulfonic acid, 4-methyl-benzene-sulfonic acid, and so forth, according to well-known techniques;
- the metal complexes obtained by the complexation reaction between the derivatives of (I) type with an either organic or inorganic metal salt such as a halide, a nitrate, a sulfate, a phosphate, e.g., of copper, manganese, zinc or iron, according to well-known techniques.

The compounds falling within the scope of the general formula (I) can be prepared by substantially known, i.e., conventional methods, which may anyway show different alternative routes.

A preferred method can be schematically represented as follows (for n=1):

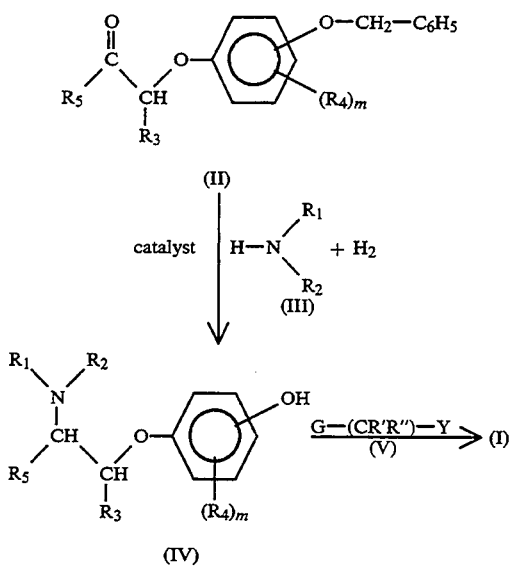

In greater detail, the carbonyl compound (II) is hydrogenated in the presence of the amine (III) and of a usual hydrogenation catalyst (Pd on charcoal, Raney-nickel) to obtain the aminic compound (IV). Hydrogen pressure can be comprised within the range of from 1 to 10 atmospheres, and the temperature can be comprised within the range of from about 0° C. to about 60° C. (see J. March "Advanced Organic Chemistry", 2nd Edition, Int. St. Edition, page 819).

In the preparation scheme reported above, the symbols $R_1$, $R_2$, $R_3$, $R_4$, $R_5$, $R'$, $R''$, and m have the previously defined meanings.

From the amine (IV), the compound (I) is obtained by reacting said amine with the compound (V), in which G assumes the meaning of halogen (Cl, Br, I), or of activated ester (methane-sulfonate, p-toluene-sulfonate), in the presence of an organic base (triethylamine, pyridine) or inorganic base (sodium carbonate, sodium bicarbonate), in protic solvents (water, ethanol) or dipolar aprotic solvents (N,N-dimethyl-formamide, N-methyl-pyrrolidone), at temperatures comprised within the range of from 25° C. up to about the boiling temperature of the solution (see J. March "Advanced Organic Chemistry", 2nd Edition, Int. St. Edition, page 357).

If desired, from the compounds (I) the corresponding metal salts and/or complexes can be prepared according to well-known techniques.

The carbonyl compounds (II) are in general easily available from the market, or can be prepared according to known techniques, The compounds (V) are easily available from the market; in the event that the symbol Y means

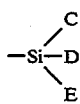

and at least one of the radicals C, D, E is ($C_1$-$C_4$)-perfluoroalkyl, then the compound (V) can be obtained according to methods known from literature [JACS 73 3518 (1951), Te. Le. 25 2195 (1984)].

The amines (III) are products available from the market, or they can be easily obtained by synthesis (see J. March "Advanced Organic Chemistry", 2nd Edition, Int. St. Edition, page 357).

The compounds of general formula (I) are endowed with high activities as inhibitors of the growth of several species of pathogen fungi which attack the cultivations of useful plants.

When they are applied to useful plants or to parts of useful plants, such e.g., to leaves, the compounds of formula (I) show both a preventive and a curative activity, and have proved themselves to be particularly effective in preventing the diseases caused by pathogen fungi, such as, e.g., those belonging to Erysiphe and Helminthosporium genera.

Examples of plant diseases which can be combated by the compounds according to the present invention are the following:

*Erysiphe graminis* on cereals,
*Sphaeroteca fuliginea* on Cucurbitaceae (e.g., cucumber),
*Puccinia* on cereals,
*Septoria* on cereals,
*Helminthosporium* on cereals,
*Rhynchosporium* on cereals,
*Podosphaera leucotricha* on apple-tree,
*Uncinula necator* on vines,
*Venturia inaequalis* on apple-tree,
*Pyricularia oryzae* on rice,
*Botrytis cinerea*,
*Fusarium* on cereals, and still other diseases.

For practical uses in agriculture, it is often useful to have available fungicidal compositions containing one or more compounds of formula (I) as active substances.

The application of these compositions may take place on each part of the plant, such as, e.g., leaves, stems, branches and roots, or on the same seeds, before seeding, or also on the soil on which the plant grows. The compositions can be used in the form of dry powders, wettable powders, emulsifiable concentrates, pastes, granulates, solutions, suspensions, and the like: the selection of the type of composition will depend on the specific use.

The compositions are prepared in a known way, for example either diluting or dissolving the active substance with a solvent medium and/or a solid diluent, possibly in the presence of surfactants. As solid diluents, or supports, the following may be used: silica, kaolin, bentonite, talc, fossil meal, dolomite, calcium carbonate, magnesium oxide, gypsum, clays, synthetic silicates, attapulgite, sepiolite.

The liquid diluents may be, of course beside water, various types of solvents, such as, e.g., aromatic solvents (benzene, xylenes or mixtures of alkyl-benzenes), chloroaromatic compounds (chlorobenzene), paraffins (petroleum cuts), alcohols (methanol, propanol, butanol), amines, amides (dimethylformamide), ketones (cyclohexanone, acetophenone, isophorone, ethyl-amyl-ketone), esters (isobutyl acetate).

As the surfactants, the following may be used: salts of sodium, calcium or triethanolamine of alkyl-sulfates, alkyl-sulfonates, alkyl-aryl-sulfonates, polyethoxylated alkyl-phenols, adducts of ethylene oxide on fatty alcohols, polyethoxylated fatty acids, polyethoxylated sorbitol esters, polyethoxylated fats, ligno-sulfonates.

The compositions may also contain special additives for particular purposes, such as, e.g., bonding agents as gum arabic, polyvinyl alcohol, polyvinylpyrrolidone.

If so desired, to the compositions according to the present invention, also other compatible active substances such as fungicides, plant growth regulants, herbicides, insecticides, fertilizers can be added.

The concentration of active substance in above said compositions may be comprised within a wide range, as a function of the active compound, of the cultivation, of the pathogen agent, of environmental conditions and of the type of formulation adopted. In an at all general way, the concentration of active substance will be comprised within the range of from 0.1% to 95% and preferably of from 0.5% to 90% (all percentages by weight).

EXAMPLES

The following Examples illustrate the invention.

Example 1

Synthesis of 4-{3-[4-(trimethylsilylmethoxy)-phenyl]-2-methyl-3-oxapropyl}-2,6-dimethyl-morpholine (Compound No. 1)

2.6 g of 4-[3-(4-idroxy-phenyl)-2-methyl-3-oxapropyl]-2,6-dimethyl-morpholine is dissolved in 10 cc of dimethylformamide. To the resulting solution 5.5 g of anhydrous sodium carbonate is added, the resulting mixture is heated to 80° C. under a nitrogen blanketing atmosphere, and is kept heated at this temperature for 30 minutes. Then 0.6 g of potassium iodide and 2.4 g of chloromethyl-trimethyl-silane are added and the mixture is heated for a further 4 hours. The reaction mixture is quenched by pouring in water and is submitted to an extraction with ethyl ether. The ethereal extract is then thoroughly dehydrated and evaporated under a reduced pressure. The resulting raw product is purified by chromatography on silica gel, with hexane/ethyl acetate=9:1 as the eluent. 2.3 g of compound 1 is obtained.

Analysis: nmr (60 Mhz) in $CDCl_3$: $\delta$=6.7 (4H, m) 4.3 (1H, m) 3.5 (4H, m) 0.8–2.8 (15H, m) 0.0 (9H, s)

Example 2

By operating in a similar way, starting from the corresponding raw materials, the compounds 2-10 were synthetized. The analytical characteristics of such compounds, determined by N.M.R., are also reported.

Compound No. 2

4-{3-[3-(2-(4,6-dichloro)-pyridyloxy)-phenyl]-2-methyl-3-oxapropyl}-2,6-dimethyl-morpholine nmr (60 Mhz) in $CDCl_3$: $\delta$=8.0 (1H, d) 7.7 (1H, d) 6.9 (4H, m) 4.3 (1H, m) 3.6 (2H, m) 0.8–2.8 (15H, m)

Compound No. 3

4-{3-[3-(2,2-di-chloro-1-methyl-cyclopropyl-methoxy)-phenyl]-2-methyl-3-oxapropyl}-2,6-dimethyl-morpholine.

nmr (60 Mhz) in $CDCl_3$: $\delta$=6.8 (4H, m) 4.3 (1H, m) 4.0 (2H, s) 3.6 (2H, m) 0.9–2.8 (20H, m)

Compound No. 4

4-[3-(5-trifluoromethylpyridyloxy-2-yl)phenyl-2-methyl-3-oxapropyl]-2,6-dimethylmorpholyne.

NMR (6 Mhz) in $CDCl_3$: =8.4 (1H, m) 7.8 (1H, m) 7.4–6.6 (5H, m) 4.4 (1H, m) 3.5 (2H, m) 2.9–0.8 (15H, m)

Compound No. 5

4-[3-(3-chloro-5-trifluoromethylpyridyloxy-2-yl)-phenyl-2-methyl-3-oxapropyl]-2,6-dimethylmorpholine.

NMR (60 Mhz) in $CDCl_3$: =8.2 (1H, m) 7.8 (1H, m) 7.3–6.5 (4H, m) 4.4 (1H, m) 3.5 (2H, m) 2.9–0.8 (15H, m)

Compound No. 6

4-[4-(dimethylphenylsilylmethoxy)-phenyl-2methyl-3-oxapropyl]-2,6-dimethylmorpholine.

NMR (60 Mhz) in $CDCl_3$: =7.8–7.2 (6H, m) 6.9 (3H, s) 4.4 (1H, m) 3.6 (4H, m+s) 2.8–0.8 (15H, m) 0.4 (6H, s)

Compound No. 7

4-[3-dimethylphenylsilylmethoxy)-phenyl-2-methyl-3-oxapropyl]-2.6-dimethylmorpholine.

NMR (60 Mhz) in $CDCl_3$: =7.7–6.8 (7H, m) 6.4 (2H, m) 4.4 (1H, m) 3.6 (4H, m+s) 2.8–0.8 (15H, m) 0.3 (6H, s)

Compound No. 8

4-[3-[-1-(trymethylsilyl)ethoxy]phenyl-2-methyl-3-oxapropyl]-2,6-dimethylmorpholine.

NMR (60 Mhz) in $CDCl_3$: =7.1 (1H, m) 6.5 (3H, m) 4.5 (1H, m) 4.0 (1H, q) 3.6 (2H, m) 2.9–0.8 (18H, m) 0.0 (9H, s)

Compound No. 9

4-[4-[-1-(trimethylsilyl)-ethoxy]phenyl-2-methyl-3-oxapropyl]-2,6-dimethylmorpholine.

NMR (60 Mhz) in $CDCl_3$: =6.8 (4H, m) 4.4 (1H, m) 3.9 (1H, q) 3.6 (2H, m) 2.9–0.9 (18H, m) 0.0 (9H, s)

Compound No. 10

4-[3-[1-(trimethylsilyl)ethoxy]phenyl-2-methyl-3-oxapropyl]-2,6-dimethylmorpholine.

NMR (60 Mhz) in $CDCl_3$: =7.1 (1H, m) 6.5 (3H, m) 4.5 (1H, m) 4.0 (1H, q) 3.6 (2H, m) 2.9–0.8 (18H, m) 0.0 (9H, s)

Example 3

Determination of the Preventive Fungicidal Activity on *Helminthosporium teres*

Both faces of leaves of plants of barley cv. Arna, grown in pots in a conditioned atmosphere, were sprayed with the investigated products (Compounds Nos. 1 and 2) in water-acetonic solution at 20% of acetone (volume/volume).

After a stay of 2 days in an atmosphere conditioned at 20° C. and 70% R.H., both faces of the leaves of the plants were sprayed with an aqueous suspension of *Helminthosporium teres* (250,000 conidia/cc). After a stay of 24 hours in an atmosphere saturated with humidity, at 21° C., the plants were stored in a conditioned environment for fungus incubation.

At the end of said time (12 days), the severity of the infection was estimated visually, and scores were assigned on the basis of a scale ranging from 100 (healthy plant) down to 0 (completely infected plant)

The data obtained is summarized in Table 1.

TABLE 1

| COMPOUND No. | DOSIS (ppm) | HELMINTHOSPORIUM CONTROL, % |
|---|---|---|
| 1 | 500 | 100 |
|   | 125 | 100 |
| 2 | 500 | 100 |
|   | 125 | 100 |

Example 4

Determination of the Fungicidal Activity on Corn Oidium (*Erysiphe graminis* D.C.)

Preventive Activity

Both faces of leaves of plants of corn cv. Irnerio, grown in pots in a conditioned environment, were sprayed with the investigated products (Compounds Nos. 1 and 2) in water-acetonic solution at 20% of acetone (volume/volume).

After a stay of 1 day in an atmosphere conditioned at 20° C. and 70% R.H., both faces of the leaves of the plants were sprayed with an aqueous suspension of *Erysiphe graminis* (200,000 conidia/cc). After a stay of 24 hours in an atmosphere saturated with humidity, at 21° C., the plants were stored in a conditioned atmosphere for fungus incubation.

At the end of said incubation time (12 days), the severity of the infection was estimated visually, and scores were assigned on the basis of a scale ranging from 100 (healthy plant) down to 0 (completely infected plant)

Curative Activity

Both faces of leaves of plants of corn cv. Irnerio, grown in pots in a conditioned atmosphere, were sprayed with an aqueous suspension of *Erysiphe graminis* (200,000 conidia/cc). After a stay of 24 hours in an atmosphere saturated with humidity, at 21° C., the leaves were sprayed with the investigated products (Compounds Nos. 1 and 2) in water-acetonic solution at 20% of acetone (volume/volume).

At the end of fungus incubation time (12 days), the severity of the infection was estimated visually, and scores were assigned on the basis of a scale ranging from 100 (healthy plant) down to 0 (completely infected plant).

The data obtained is summarized in Table 2.

TABLE 2

| COMPOUND No. | DOSIS (ppm) | ERYSIPHE CONTROL, % |
|---|---|---|
| 1 | 500 | 100 |
|   | 250 | 100 |
|   | 125 | 100 |
| 2 | 500 | 100 |
|   | 250 | 100 |
|   | 125 | 100 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Antifungal compounds useful in agriculture having the formula:

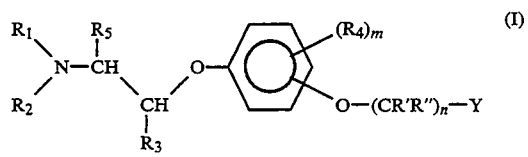

wherein:

$R_1$ and $R_2$, taken together with each other and the N atom represent a morpholine or thiomorpholine group, which groups can be optionally substituted with at least one group selected from among $(C_1-C_4)$-alkyl, $(C_6$ or $C_{10})$-aryl, Ar—B groups, in which Ar is a phenyl group optionally halogenated and B is a $(C_1-C_4)$ alkylene or $(C_1-C_2)$-alkyl-$(C_1-C_4)$-alkylene group and halogen atoms;

$R_3$ and $R_5$, which may be either the same, or different from, each other, represent H atoms, $(C_1-C_3)$-alkyl groups, or jointly form an either linear or branched $(C_1-C_7)$-alkylene group;

m is an integer of from 0 to 4;

$R_4$ represent a halogen atom, $(C_1-C_3)$-alkyl groups or $(C_1-C_3)$-halo-alkyl groups, and when m is greater than 1, $R_4$ as defined above, may be the same, or different from one another;

R', R'', which may be the same, or different from, each other, represent H, $(C_1-C_3)$-alkyl groups, or halogen atoms;

n is an integer from 0 to 3;

Y represents a —CH=CH$_2$ group, a $(C_3-C_6)$-cycloalkyl group, pyridine or pyrimidine, and said groups can be optionally substituted with at least one group selected from halogen, $(C_1-C_4)$-alkyl groups, $(C_1-C_2)$-haloalkyl groups, $(C_1-C_3)$-alkoxy groups, and $(C_1-C_3)$-haloalkoxy groups; or represents a

group in which C, D, E, either the same, or different from, one another, represent H atoms, $(C_1-C_4)$-alkyl groups, $(C_1-C_4)$-haloalkyl groups, $(C_1-C_4)$-alkoxy groups, or $(C_1-C_4)$-haloalkoxy groups; their enantiomers and diastereoisomers.

2. Compounds according to claim 1 wherein said morpholine or thiomorpholine group is 2,6-dimethyl-morpholine, the dimethyl-morpholine being optionally substituted with halogen atoms, $(C_1-C_4)$-alkyl groups, $(C_6$ or $C_{10})$-aryl groups or, Ar13 B groups in which Ar is a phenyl group optionally halogenated and B is a $(C_1-C_4)$-alkylene or $(C_1-C_2)$-alkyl-$(C_1-C_4)$-alkylene group.

3. Compounds according to claim 1, wherein said morpholine or thiomorpholine group is substituted with at least one group selected from among $(C_1-C_4)$alkyl, $(C_6$ or $C_{10})$-aryl, Ar—B groups, in which Ar is a phenyl group optionally halogenated and B is a $(C_1-C_4)$ alkylene or $(C_1-C_2)$-alkyl-$(C_1-C_4)$-alkylene group and halogen atoms.

4. Antifungal compounds useful in agriculture having the formula:

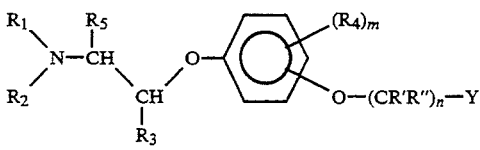

wherein:
- $R_1$ and $R_2$, taken together with each other and the N atom represent a morpholine or thiomorpholine group;
- $R_3$ and $R_5$, which may be either the same, or different from, each other, represent H atoms, $(C_1-C_3)$-alkyl groups, or jointly form an either linear or branched $(C_1-C_7)$-alkylene group;
- m is an integer of from 0 to 4;
- $R_4$ represent a halogen atom, $(C_1-C_3)$-alkyl groups or $(C_1-C_3)$-halo-alkyl groups and, when m is greater than 1, $R_4$ as defined above, may be either different from, or the same as one another;
- $R'$, $R''$, which may be the same, or different from, each other, represent H, $(C_1-C_3)$-alkyl groups, or halogen atoms;
- n is an integer from 0 to 3;
- Y represents a pyridine, pyrimidine, thiophene, thiazole, oxazole, isoxazole group, a cyclohexyl, cyclopropyl, cyclopentyl, cyclobutyl, 1-methyl-2,2-dichlorocyclopropyl, trimethyl-silyl, tert-butyl-dimethyl-silyl or dimethyl-phenyl-silanyl group.

5. Antifungal compounds useful in agriculture having the formula:

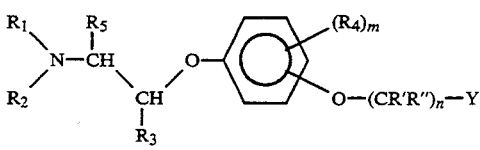

wherein:
- $R_1$ and $R_2$, taken together with each other and the N atom represent a morpholine or thiomorpholine group;
- $R_3$ and $R_5$, which may be either the same, or different from, each other, represent H atoms, $(C_1-C_3)$-alkyl groups, or jointly form an either linear or branched $(C_1-C_7)$-alkylene group;
- m is an integer of from 0 to 4;
- $R_4$ represent a halogen atom, $(C_1-C_3)$-alkyl groups or $(C_1-C_3)$-halo-alkyl groups, and when m is greater than 1, $R_4$ as defined above, may be either different from, or the same as one another;
- $R'$, $R''$, which may be the same, or different from, each other, represent H, $(C_1-C_3)$-alkyl groups, or halogen atoms;
- n is an integer from 0 to 3;
- Y represents an ethenyl, a $(C_3-C_6)$-cycloalkyl, or pyridine or pyrimidine group that is substituted with at least one group selected from among $(C_1-C_4)$-alkyl, $(C_1-C_2)$-haloalkyl groups, $(C_1-C_3)$-alkoxy groups, $(C_1-C_3)$ haloalkoxy groups and halogen atoms.

6. Compound according to claim 4, which is 4-{3-[4-(trimethylsilylmethoxy)phenyl]-2-methyl-3-oxapropyl}-2,6-dimethyl-morpholine.

7. Compound according to claim 5, which is 4-{3-[3-(2-(4,6-dichloro)-pyridyloxy)-phenyl]-2-methyl-3-oxapropyl}-2,6-dimethyl-morpholine.

8. Compound according to claim 5, which is 4-{3-[3-(2,2-dichloro-1-methyl-cyclopropylmethoxy)phenyl]-2-methyl-3-oxapropyl}-2,6-dimethyl-morpholine.

9. Compound according to claim 5, which is 4-[3-(5-trifluoromethylpyridyloxy-2-yl )phenyl-2-methyl-3-oxapropyl]-2,6-dimethyl-morpholine.

10. Compound according to claim 5, which is 4-[3-(3-chloro-5-trifluoromethylpyridyloxy-2-yl)phenyl-2-methyl-3-oxapropyl]-2,6-dimethyl-morpholine.

11. Compound according to claim 4, which is 4-[4-(dimethylphenylsilylmethoxy)-phenyl-2-methyl-3-oxapropyl]-2,6-dimethyl-morpholine.

12. Compound according to claim 4, which is 4-[3-(dimethylphenylsilylmethoxy)-phenyl-2-methyl-3-oxapropyl]-2,6-dimethylmorpholine.

13. Compound according to claim 4, which is 4-[3-[-1-(trimethylsilyl)ethoxy]phenyl-2-methyl- 3 -oxapropyl]-2,6-dimethylmorpholine.

14. Compound according to claim 4, which is 4-[4-[-1-(trimethylsilyl)-ethoxy]phenyl-2-methyl-3-oxapropyl]-2,6-dimethyl-morpholine.

15. Compound according to claim 4, which is 4-[3-[-1-(trimethylsilyl)ethoxy]phenyl 2-methyl-3-oxapropyl]-2,6-dimethyl-morpholine.

16. Antifungal compounds useful in agriculture having the formula:

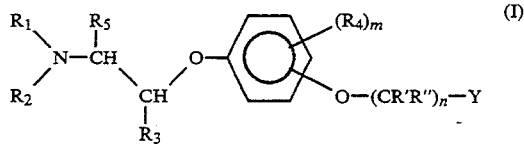

wherein:
- $R_1$ and $R_2$, taken together with each other and the N atom represent a morpholine or thiomorpholine group;
- $R_3$ and $R_5$, which may be either the same, or different from, each other, represent H atoms, $(C_1-C_3)$-alkyl groups, or jointly form an either linear or branched $(C_1-C_7)$-alkylene group;
- m is an integer of from 0 to 4;
- $R_4$ represent a halogen atom, $(C_1-C_3)$-alkyl groups, or $(C_1-C_3)$-halo-alkyl groups, and when m is greater than 1, $R_4$ as defined above, may be the same, or different from one another;
- $R'$, $R''$ which may be the same, or different from, each other, represent H $(C_1-C_3)$-alkyl groups, or halogen atoms;
- n is an integer from 0 to 3;
- Y represents a —CH=CH$_2$ group, a $(C_3-C_6)$-cycloalkyl group, pyridine or pyrimidine group, and said groups can be optionally substituted with at least one group selected from halogen, $(C_1-C_4)$-alkyl groups, $(C_1-C_2)$-haloalkyl groups, $(C_1-C_3)$-alkoxy groups, and $(C_1-C_3)$-haloalkoxy groups; or represents a

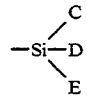

group in which C, D, E, either the same, or different from, one another, represent H atoms, $(C_1-C_4)$-alkyl groups, $(C_1-C_4)$-haloalkyl groups, $(C_1-C_4)$-alkoxy groups, or $(C_1-C_4)$-haloalkoxy groups; their enantiomers and diastereoisomers.

17. Antifungal compounds useful in agriculture having the formula:

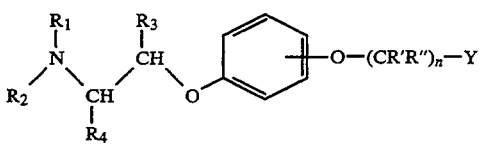

wherein $R_1$ and $R_2$ taken together with each other and the N atom represent a morpholine or 2,6-dimethyl-morpholine;

$R_3$ and $R_4$ which may be the same, or different from each other, represent H, or $(C_1-C_3)$-alkyl;

$R'$, $R''$ which may be the same, or different from each other, represent H, or $(C_1-C_3)$-alkyl;

n is an integer from 0 to 1;

Y represents $(C_3-C_6)$-cycloalkyl optionally substituted by halogen; pyridyl optionally substituted by halogen or $(C_1-C_2)$-haloalkyl; trimethylsilyl; or dimethylphenylsilyl.

18. Method of using aryl-propyl-aminic antifungal compounds as inhibitor agents inhibiting the growth of pathogen fungi in the cultivations of useful plants comprising applying an effective amount of said compounds to said cultivations, said compounds having the formula:

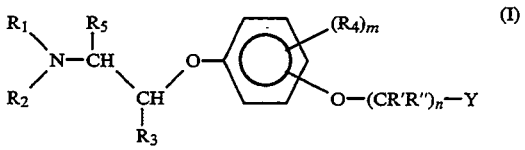

wherein:

$R_1$ and $R_2$, taken together with each other and the N atom represent a morpholine or thiomorpholine group;

$R_3$ and $R_5$, which may be either the same, or different from, each other, represent H atoms, $(C_1-C_3)$-alkyl groups, or jointly form an either linear or branched $(C_1-C_7)$-alkylene group;

m is an integer of from 0 to 4;

$R_4$ represent a halogen atom, $(C_1-C_3)$-alkyl groups or $(C_1-C_3)$-halo-alkyl groups, and when m is greater than 1, $R_4$ as defined above, may be the same, or different from one another;

$R'$, $R''$, which may be the same, or different from, each other, represent H, $(C_1-C_3)$-alkyl groups, or halogen atoms;

n is an integer from 0 to 3;

Y represents a $—CH=CH_2$ group, a $(C_3-C_6)$-cycloalkyl group, pyridine or pyrimidine group, and said groups can be optionally substituted with at least one group selected from halogen, $(C_1-C_4)$-alkyl groups, $(C_1-C_2)$-haloalkyl groups, $(C_1-C_3)$-alkoxy groups, and $(C_1-C_3)$-haloalkoxy groups; or represents a

group in which C, D, E, either the same, or different from, one another, represent H atoms, $(C_1-C_4)$-alkyl groups, $(C_1-C_4)$-haloalkyl groups, $(C_1-C_4)$-alkoxy groups, or $(C_1-C_4)$-haloalkoxy groups; their enantiomers and diastereoisomers.

19. A method of inhibiting fungi belonging to the class of Erysiphe and Helminthosporium genera comprising applying an effective amount of an agricultural antifungal composition to cultivars to inhibit the growth of the pathogen fungi belonging to Erysiphe and Helminthosporium genera, said composition comprising a compound of the formula:

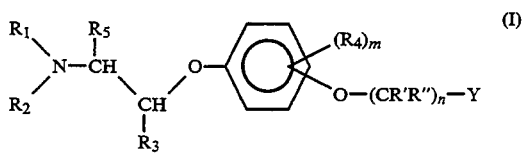

wherein:

$R_1$ and $R_2$, taken together with each other and the N atom represent a morpholine or thiomorpholine group;

$R_3$ and $R_5$, which may be either the same, or different from, each other, represent H atoms, $(C_1-C_3)$-alkyl groups, or jointly form an either linear or branched $(C_1-C_7)$-alkylene group;

m is an integer of from 0 to 4;

$R_4$ represent a halogen atom, $(C_1-C_3)$-alkyl groups or $(C_1-C_3)$-halo-alkyl groups, and when m is greater than 1, $R_4$ as defined above, may be the same, or different from one another;

$R'$, $R''$, which may be the same, or different from, each other, represent H, $(C_1-C_3)$-alkyl groups, or halogen atoms;

n is an integer from 0 to 3;

Y represents a $—CH=CH_2$ group, a $(C_3-C_6)$-cycloalkyl group, pyridine or pyrimidine group, and said groups can be optionally substituted with at least one group selected from halogen, $(C_1-C_4)$-alkyl groups, $(C_1-C_2)$-haloalkyl groups, $(C_1-C_3)$-alkoxy groups, and $(C_1-C_3)$-haloalkoxy groups; or represents a

group in which C, D, E, either the same, or different from, one another, represent H atoms, $(C_1-C_4)$-alkyl groups, $(C_1-C_4)$-haloalkyl groups, $(C_1-C_4)$-alkoxy groups , or $(C_1-C_4)$-haloalkoxy groups; their enantiomers and diastereoisomers; in an agriculturally acceptable carrier.

* * * * *